United States Patent
Delmas et al.

(10) Patent No.: US 8,551,747 B2
(45) Date of Patent: Oct. 8, 2013

(54) PROCESS FOR PRODUCING BIOETHANOL FROM LIGNOCELLULOSIC PLANT RAW MATERIAL

(75) Inventors: Michel Delmas, Auzeville-Tolosane (FR); Bouchra Benjelloun Mlayah, Pompertuzat (FR)

(73) Assignee: Campagnie Industrielle de la Matiere Vegetale CIMV, Levallois-Perret (FR)

( * ) Notice: Subject to any disclaimer, the term of this patent is extended or adjusted under 35 U.S.C. 154(b) by 376 days.

(21) Appl. No.: 12/863,597

(22) PCT Filed: Jan. 22, 2009

(86) PCT No.: PCT/EP2009/050690
§ 371 (c)(1),
(2), (4) Date: Jul. 20, 2010

(87) PCT Pub. No.: WO2009/092749
PCT Pub. Date: Jul. 30, 2009

(65) Prior Publication Data
US 2010/0285553 A1 Nov. 11, 2010

(30) Foreign Application Priority Data
Jan. 25, 2008 (FR) ..................... 08 50458

(51) Int. Cl.
C12P 7/06 (2006.01)
C12P 7/14 (2006.01)
C12P 7/08 (2006.01)
C12P 7/10 (2006.01)

(52) U.S. Cl.
USPC ............ 435/161; 435/162; 435/163; 435/165

(58) Field of Classification Search
None
See application file for complete search history.

(56) References Cited

U.S. PATENT DOCUMENTS

| 6,022,419 | A * | 2/2000 | Torget et al. ............ 127/37 |
| 6,183,597 | B1 | 2/2001 | Siegle |
| 7,402,224 | B1 | 7/2008 | Avignon et al. |
| 7,943,350 | B2 * | 5/2011 | Vlasenko et al. ....... 435/101 |
| 8,101,393 | B2 * | 1/2012 | Gray et al. ............. 435/209 |
| 8,157,964 | B2 * | 4/2012 | Benjelloun Mlayah et al. ............. 162/237 |

FOREIGN PATENT DOCUMENTS

| DE | 195 16 151 A1 | 11/1996 |
| EP | 0 584 675 A1 | 3/1994 |
| WO | 95/21960 A1 | 8/1995 |
| WO | 00/68494 A1 | 11/2000 |

OTHER PUBLICATIONS

International Search Report, dated Mar. 19, 2009, from corresponding PCT application.

\* cited by examiner

*Primary Examiner* — David M Naff
(74) *Attorney, Agent, or Firm* — Young & Thompson

(57) ABSTRACT

A process for pretreating a lignocellulosic plant raw material in order to obtain a pretreated material that is capable of being hydrolyzed and fermented for the production of bioethanol, includes the following successive steps:

(i) destructuring the lignocellulosic plant raw material by placing it in the presence of a mixture containing formic acid and water, at a reaction temperature between 95° C. and 110° C.;

(ii) then, at atmospheric pressure and prior to any hydrolysis then fermentation action, separating:
  on the one hand, the solid phase, mainly composed of the cellulose, constituting a first co-substrate, capable of then being hydrolyzed and fermented for the production of bioethanol; and
  on the other hand, the liquid phase, containing, in particular in aqueous solution, the formic acid, the lignins, and the hemicelluloses, constituting a second co-substrate, capable of then being hydrolyzed and fermented for the production of bioethanol.

7 Claims, No Drawings

PROCESS FOR PRODUCING BIOETHANOL FROM LIGNOCELLULOSIC PLANT RAW MATERIAL

TECHNICAL FIELD OF THE INVENTION

The present invention relates to a process for pretreating lignocellulosic plant material with a view to producing bioethanol, or ethanol, and lignins.

The present invention relates to a process for pretreating lignocellulosic plant material constituting the essential part of annual and perennial plants.

In what follows, the expression "annual plant" is understood to mean any plant having a vegetative life of the order of one year (cereals, various grasses, cotton, hemp, flax, sorghum, sugar cane, reeds, etc.) and the expression "perennial plant" is understood to mean a plant whose development extends over a longer period, (bamboos, hardwoods, softwoods, etc.).

The lignocellulosic plant raw materials to which the invention applies are whole plants or parts of these plants (stems, bark, etc.) or co-products from industrial processes aimed at the production of foods, (wheat straw, rice, barley; sugar cane bagasse, sugar sorghum bagasse, etc.).

TECHNICAL BACKGROUND OF THE INVENTION

The production of bioethanol from the lignocellulose that constitutes the wall of plants is today an important issue on account of:
- the availability of lignocellulosic plant raw material (cereal straw, sugar cane bagasse, wood, etc.);
- the increase in the cost of fossil energies and especially oil and the necessity that follows therefrom to have substitutes for some of the refined petroleum products, in particular for their use as fuels; and
- the recent and very high increase in the cost of cereals due, for the main part, to the competition between the s conventional food sector and the production of bioethanol from grains.

Lignocellulose is a generic term that denotes the natural composite material that gives shape and structure to plants. It is the combination of three natural biopolymers, which are:
- cellulose, which is a stereoregular polysaccharide resulting from the polymerization of D-glucose to $\beta$-1,4-glucose;
- lignins, which are polyphenols resulting from the polymerization of phenolic allyl alcohols; and
- hemicelluloses, which are polysaccharides resulting from is the polymerization of sugars having 5 (five) carbon atoms such as xylose and arabinose and/or having 6 (six) carbon atoms such as glucose and mannose.

The proportion and the distribution of the various sugars depends on the plant in question.

Thus, the hemicelluloses of annual plants and of hardwoods have, in a very large proportion, xylose as the main monomer, whereas the main monomer of hemicelluloses of softwoods is mannose.

These three macromolecules are arranged as supramolecular and anatomical structures that are much more complex than the structure of starch granule or of free sucrose, which explains why the utilization of lignocelluloses in the form of bioethanol raises specific problems especially on an industrial scale.

The cellulose and hemicelluloses from these plants are the essential part of terrestrial biomass. These two biopolymers therefore constitute an enormous reserve of fermentable sugars on a worldwide scale, which bears no comparison with the glucose derived from the fermentation of starch, of cereal grains or of potatoes.

Depending on the initial plant raw material, the process for producing bioethanol generally comprises three large main sets of s operations, that is to say, consecutively A) the preparation of a wort, then B) the fermentation of the wort for the purpose of obtaining a fermented wort, then D) the distillation of the fermented wort for the purpose of producing bioethanol.

To these three large sets of operations, it is possible to add a fourth general set of operations E) that consists of the various treatments of the co-products resulting from each of these three main sets of operations.

All the operations A) for preparing the wort aim to prepare a paste or a liquor comprising the plant raw material capable of is being fermented, that is to say an aqueous solution of sugars that can be fermented by yeasts, by aiming to obtain the highest possible concentration so as to reduce the capacities of the equipment necessary for preparing the wort and for other subsequent operations. In the case of production from lignocellulosic resources, the conversion of the cellulose and hemicelluloses to ethanol requires a prior incontrovertible "step" of depolymerization to sugar monomers, followed by their fermentation.

Since the 1980's, it has thus appeared that solving problems specific to the production from lignocellulosic resources imposed the optimal functioning of the following steps.
LIGNOCELLULOSES→Pretreatment→CELLULOSE+ LIGNINS→(Enzymatic) hydrolysis→GLUCOSE+ LIGNINS→Fermentation→Distillation→ETHANOL/BIOETHANOL Although the fermentation operation has been known since the first conversion of a sugary liquor to an alcoholic drink and is therefore carried out annually on tens of millions of metric tons, the same is not true for the pretreatment of cellulose which, to date, has no profitable industrial application in the world.

For more than half a century, numerous studies have been carried out that relate to pretreating plant material so as to make s the cellulose able to be hydrolyzed to glucose under industrially acceptable conditions.

None of the processes studied have to date actually succeeded on an industrial scale, despite the tremendous means that have been dedicated thereto.

These known pretreatments generally proceed via a first dissolution in water of some of the hemicelluloses in the form of monomers, oligomers and polymers in acid or basic medium.

The lignocellulose is then treated so as to obtain monosaccharides, oligosaccharides, or even polysaccharides that is can be easily fermented by pretreatments via:
- acid hydrolysis of the polysaccharides under "harsh" conditions at high temperatures (120 to 250° C.) and under high pressures with concentrations of acids that may range up to 12 wt %;
- steam explosion at high pressures (1 to $3 \times 10^6$ Pa) and high temperatures (190 to 220° C.);
- addition of an organic solvent that facilitates the destructuring of the plant in question; and
- enzymatic hydrolysis followed by fermentation of the hydrolyzate, combined with an ultrasound treatment.

All of these known pretreatments certainly facilitate the conversion of cellulose to alcohol, but have the major drawback of producing a polysaccharide-contaminated ligneous residue that is then difficult to utilize other than by incineration.

These lignins furthermore have the drawback of interfering with the action of enzymes during the hydrolysis step that follows the pretreatment, especially on account of the presence of lignins and of furfural present in most acid prehydrolyses.

Furthermore, this type of pretreatment results in a significant cost, which is prohibitive on an industrial scale, especially on account of the investment in equipment and of the need to use steam.

SUMMARY OF THE INVENTION

In order to overcome these drawbacks, the process according to the invention provides a radically different approach by carrying out a separation of the three biopolymers by solvolysis in an acid/aqueous medium, which makes it possible to separate linear, non-recombined, low molecular weight and high value added lignins, prior to any action of hydrolysis then of fermentation of the cellulose and the hemicelluloses.

The invention thus relates to a process that makes it possible to obtain industrial performances regardless of the nature of the plants used and which is therefore particularly advantageous in the case of annual plants for opening the way to a new valorization, especially in the case of cereal straws, and sugar cane bagasse or sugar sorghum bagasse, a valorization that is added to that already proposed by the applicant in international application WO-A1-00/68494, which relates to a method for producing paper pulp, lignins, sugars and acetic acid by fractionation of lignocellulosic plant material in a formic acid/acetic acid medium.

For this purpose, the invention provides a process for pretreating a lignocellulosic plant raw material that aims to separate the cellulose, hemicelluloses and lignins contained in this lignocellulosic plant raw material, in order to obtain a pretreated material that is capable of being hydrolyzed and fermented for the production of bioethanol, characterized in that it comprises the following successive steps that consist in:
  (i) destructuring the lignocellulosic plant raw material by placing it in the presence of a mixture containing formic acid and water, at a reaction temperature between 95° C. and 110° C.;
  (ii) then, at atmospheric pressure and prior to any hydrolysis then fermentation action, in separating:
    on the one hand, the solid phase, mainly composed of said cellulose, constituting a first co-substrate, capable of then being hydrolyzed and fermented for the production of bioethanol; and
    on the other hand, the liquid phase, containing, in particular in aqueous solution, the formic acid, the lignins, and the hemicelluloses—more or less solubilized, constituting a second co-substrate, capable of then being hydrolyzed and is fermented for the production of bioethanol.

By virtue of the pretreatment process according to the invention that requires a precise range of reaction temperature values, the following are obtained—from the lignocellulosic plant raw material—for the first time, under industrial and economic conditions and simultaneously, two co-substrates, or substrates, capable of being hydrolyzed including:
  a) a first co-substrate composed of ground cellulose, that is to say cellulose that is free of lignins and of hemicelluloses, having optimum conditions for its subsequent enzymatic hydrolysis;
  b) a second substrate composed of "sugar molasses" originating from the hemicelluloses, the hydrolyzates of which are free of furfural, and which may be separated from the other components of the liquid phase and in particular from the lignins by simple operations so that the residual lignin content of the sugar molasses is almost zero.

The process according to the invention thus goes against the known processes in which placing the plant raw material in the presence of a mineral acid at temperatures at 110° C. leads to a significant production of furfural.

Furthermore, the lignins obtained are linear, non-recombined, low molecular weight, very high quality and high s value added lignins.

The process according to the invention thus has an excellent economic balance insofar as the three major macromolecular compounds, or biopolymers, of the lignocellulosic plant raw material are utilized or are recoverable in the form of bioethanol and in the form of lignins, without there being any "pollution" between these two parts of the utilization.

According to other aspects of the invention:
  the mixture contains at least 50 wt % formic acid;
  the destructuring step (i) consists in placing the is lignocellulosic plant raw material in the presence of a mixture containing formic acid, acetic acid and water, at a reaction temperature between 95° C. and 110° C.;
  this mixture contains at least 20 wt % formic acid and at least 50 wt % acetic acid; formic acid enables the destructuring of the lignocellulosic material and makes it possible to obtain cellulose that is free of lignins and of hemicelluloses; its content depends on the lignocellulosic material to be treated; acetic acid serves as a solvent, in order to carry lignins and hemicelluloses into the liquid phase;
  the destructuring step (i) is carried out at atmospheric pressure;
  the separating step (ii) is carried out by pressing, for example using a filter press. Such a "facing" separation allows, unlike centrifugation, a perfect lignins-sugars separation;
  the process may, in addition, comprise a prior step that consists, prior to said destructuring step (i), in carrying out a prior impregnation of the lignocellulosic plant raw material at atmospheric pressure and at a temperature at least 30° C. below the reaction temperature.

The invention also provides a process for producing bioethanol from a lignocellulosic plant raw material, characterized in that it comprises, in particular, the successive steps of:
  pretreating the lignocellulosic plant raw material according to the pretreatment process as claimed in the invention in order to obtain a pretreated material that is capable of being hydrolyzed and fermented for the production of bioethanol;
  hydrolysis, especially enzymatic hydrolysis, of said pretreated material;
  alcoholic fermentation of the products from said hydrolysis step that are capable of being fermented for the production of bioethanol.

The invention claimed is:

1. A process for producing bioethanol from a lignocellulosic plant raw material, comprising the successive steps of:
  a) destructuring a lignocellulosic plant raw material by contacting the lignocellulosic plant raw material with a mixture containing formic acid and water at a temperature between 95° C. and 110° C.;
  b) separating the destructured lignocellulosic plant raw material at atmospheric pressure into a solid phase mainly composed of said cellulose constituting a first substrate, and a liquid phase containing in aqueous solution, hemicelluloses, lignins and the formic acid, constituting a second substrate;

c) hydrolysing the first and second substrates to produce a hydrolysed material;
d) fermenting the hydrolysed material to produce a fermented material containing ethanol; and
e) distilling ethanol from the fermented material to produce bioethanol.

2. The process as claimed in claim 1, wherein said mixture of said destructuring step a) contains at least 50 wt% formic acid.

3. The process as claimed in claim 2, wherein said mixture of said destructuring step a) contains the formic acid, acetic acid and water.

4. The process as claimed in claim 3, wherein said mixture contains at least 20 wt% formic acid and at least 50 wt% acetic acid.

5. The process as claimed in claim 1, wherein said destructuring step a) is carried out at atmospheric pressure.

6. The process as claimed in claim 1, wherein said separating step b) is carried out by filtration using a filter press.

7. The process as claimed in claim 1, wherein the hydrolysing step c) is carried out by enzymatic hydrolysis.

\* \* \* \* \*